US 6,645,238 B2

(12) United States Patent
Smith

(10) Patent No.: US 6,645,238 B2
(45) Date of Patent: Nov. 11, 2003

(54) SKIDS STENT DELIVERY SYSTEM

(75) Inventor: Scott R. Smith, Chaska, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/682,013

(22) Filed: Jul. 9, 2001

(65) Prior Publication Data

US 2003/0009174 A1 Jan. 9, 2003

(51) Int. Cl.7 .................................................. A61F 2/06
(52) U.S. Cl. ...................................... 623/1.11; 606/108
(58) Field of Search .............................. 623/1.11, 1.12; 606/108

(56) References Cited

U.S. PATENT DOCUMENTS

| | | | |
|---|---|---|---|
| 5,683,451 A | * | 11/1997 | Lenker et al. ............. 623/1.11 |
| 5,693,034 A | | 12/1997 | Buscemi et al. ............ 604/265 |
| 5,702,364 A | | 12/1997 | Euteneuer et al. ............ 604/96 |
| 5,772,669 A | | 6/1998 | Vrba .......................... 606/108 |
| 5,951,585 A | * | 9/1999 | Cathcart et al. ............. 606/198 |
| 5,980,533 A | | 11/1999 | Holman ...................... 606/108 |
| 6,036,697 A | | 3/2000 | DiCaprio .................... 606/108 |
| 6,213,995 B1 | * | 4/2001 | Steen et al. ................. 604/527 |
| 6,270,521 B1 | * | 8/2001 | Fischell et al. ............. 623/1.11 |
| 6,270,522 B1 | * | 8/2001 | Simhambhatla et al. ... 623/1.11 |
| 6,478,814 B2 | * | 11/2002 | Wang et al. ................ 623/1.12 |
| 2001/0012959 A1 | * | 8/2001 | Blaeser et al. ............. 623/1.11 |
| 2002/0038140 A1 | * | 3/2002 | Yang et al. ................. 623/1.12 |
| 2002/0165598 A1 | * | 11/2002 | Wahr et al. ................. 623/1.11 |

FOREIGN PATENT DOCUMENTS

| | | |
|---|---|---|
| EP | 0 812 579 A1 | 12/1997 |
| EP | 1 025 813 A3 | 8/2000 |
| EP | 1 025 813 A2 | 8/2000 |
| EP | 1 064 888 A1 | 1/2001 |

OTHER PUBLICATIONS

U.S. patent application Ser. No. 09/668,496, Yang, filed Sep. 22, 2000.

* cited by examiner

Primary Examiner—David H. Willse
Assistant Examiner—Thomas J Sweet
(74) Attorney, Agent, or Firm—Vidas, Arrettt & Steinkraus PA

(57) ABSTRACT

A medical device delivery catheter comprises an inner member and a retractable sheath assembly disposed about the inner member. The retractable sheath assembly comprises a retractable sheath and one or more skids extending from the retractable sheath. The skids are disposed between the retractable sheath and the inner member.

22 Claims, 4 Drawing Sheets

SKIDS STENT DELIVERY SYSTEM

BACKGROUND OF INVENTION

Stents are used to maintain the patency of bodily vessels such as coronary, mesentery, peripheral, or cerebral vasculature, veins, the gastrointestinal tract, the biliary tract, the urethra, the trachea, hepatic shunts and fallopian tubes. Stents are delivered to desired locations in bodily vessel via catheters. Examples of catheters are disclosed in U.S. Pat. Nos. 5,772,669 and 6,036,697.

A schematic illustration of a prior art catheter is shown generally at 100 in FIG. 1. Catheter 100 comprises inner tube 104, stent 108 disposed about inner tube 104 toward the distal end of the catheter and retractable sheath 114 which is disposed about stent 108. Retractable sheath 114 is maintained in place over stent 108 during stent delivery to protect the bodily vessel from the stent and to generally facilitate stent delivery. Pull collar 115 is affixed to retractable sheath 114 and pull wire 113 extends proximally from pull collar 115. Upon delivery of stent 108 to the desired location, retractable sheath 114 may be retracted by pulling on pull wire 113. The stent may thus be exposed for expansion and implantation in the desired region of the vessel. Other types of retraction mechanisms are also known in the art.

Subsequent to loading a stent in the catheter, the retractable sheath may dimple or become partially embedded in portions of the stent, in particular where the stent is self-expanding. As shown in FIG. 1, portions 117 of retractable sheath 114 protrude in between struts 116 of stent 108 hampering the retraction of the sheath from over the stent and risking damage to the stent.

The problems of dimpling and/or embedding of the stent are exacerbated as thinner sheaths are used. While it is desirable to employer thinner retractable sheaths to ensure flexibility of the catheter in the region of the retractable sheath and to maintain a low catheter profile, the use of thinner sheaths increases the likelihood of dimpling and/or embedding. Dimpling of the retractable sheath and/or embedding of the retractable sheath increases the forces required to retract the sheath. Moreover, where thinner sheaths are used, loading a stent may prove difficult as a result of buckling of the sheath.

The problems of dimpling and/or embedding of the stent impact on the choice of materials for sheaths. Materials such as PTFE are desirable for use in retractable sheaths because of their low coefficients of friction, but they are particularly susceptible to dimpling and/or impressing of the stent in the materials and have not, to date, proved practical for use in retractable sheaths.

Although there have been a multitude of patents directed toward stent delivery catheters, there remains a need for innovative catheters which avoid the above-mentioned problems. There also remains a need for catheters having retractable sheaths which are formed using low coefficient of friction materials without the above mentioned disadvantages of such materials.

All U.S. patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72.

SUMMARY OF INVENTION

The instant invention is directed in one embodiment to a medical device delivery catheter comprising an inner member and a retractable sheath assembly disposed about the inner member. The retractable sheath assembly comprises an outer sheath of a first material and one or more skids. The skids comprise an outer layer of a first skid material and an inner layer of a second skid material. The second skid material is different from the first skid material. The retractable sheath assembly is constructed and arranged such that the skids are disposed between the outer sheath and the inner member prior to, during and subsequent to retraction of the retractable sheath assembly. Optionally, the catheter further comprises a stent or other medical device disposed about the inner member with the retractable sheath assembly disposed about the stent.

Desirably, the first skid material is harder than the second skid material, desirably as measured using the Shore D hardness scale. Also desirably, the second skid material is more slippery than the first skid material, desirably as measured by the coefficient of friction. Even more desirably, the first skid material is harder than the second skid material and the second skid material is more slippery than the first skid material. As an example of a suitable combination of materials, the first skid material may be a hard polymeric material such as polyimide and the second skid material is a slippery polymeric material such as PTFE. Other suitable materials for the second skid material include ceramics, amorphous carbon—desirably in the form of diamond like coatings and ceramic—for example A1O. The second skid material may line the entire interior of the sheath or may be provided in the form of skids which are adjacent one another and spaced from one another.

In yet another embodiment, the invention is directed to a medical device delivery catheter comprising an inner member and a retractable sheath assembly disposed about the inner member, the retractable sheath assembly having a bending flexibility of at least 1.17 GPa. Desirably, the retractable sheath assembly includes one or more skids. The skids comprise an outer skid layer of a first skid material and an inner skid layer of a second skid material. The outer skid layer may optionally have a shore D hardness of at least 84. The one or more skids are disposed between the sheath and the inner member. Desirably, the retractable sheath assembly further comprises a sheath disposed about the skids and attached thereto.

Additional details and/or embodiments of the invention are discussed below.

DETAILED DESCRIPTION

Figure 1:
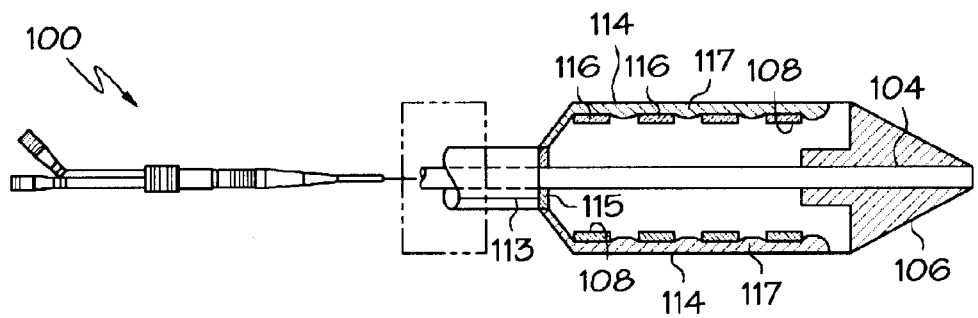
FIG. 1 is a schematic illustration of a prior art catheter.

While this invention may be embodied in many different forms, there are shown in the drawings and described in detail herein specific embodiments of the invention. The present disclosure is an exemplification of the principles of the invention and is not intended to limit the invention to the particular embodiments illustrated.

For the purposes of this disclosure, the term "comprising" means "including, but not limited to". Also, for the purposes of this disclosure, unless otherwise indicated, like reference numerals in the figures refer to the same component.

Figure 2:
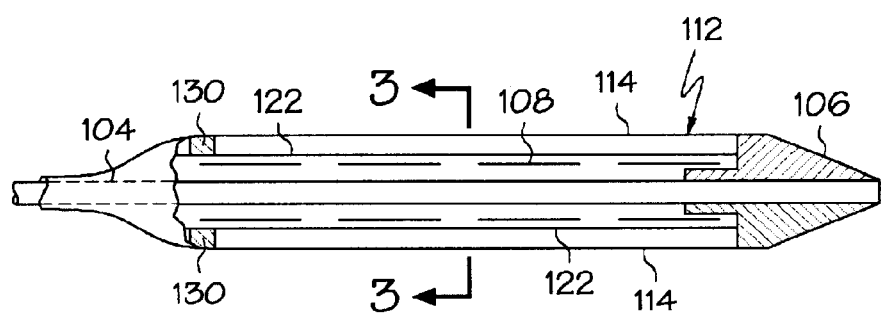
FIG. 2 is a schematic illustration of the distal end an inventive catheter.

In one embodiment, the invention is directed to a medical device delivery catheter, the distal end of which is shown in FIG. 2. The catheter comprises inner member 104 and retractable sheath assembly 112 disposed about inner member 104. Typically, inner member 104 is in the form of a tube. Inner member 104 may also be a solid, elongate structure, as for example, in the case of a fixed-wire catheter. Inner member 104 terminates in tip 106. Retractable sheath assembly 112 is disposed about optional stent 108. Other medical devices may also be provided. The catheter may further comprise one or more bumpers (not shown) and one or more marker bands (not shown) as are known in the art. The use of bumpers and marker bands is disclosed in U.S. Pat. No. 5,989,280 as well as elsewhere in the art.

Figure 3:
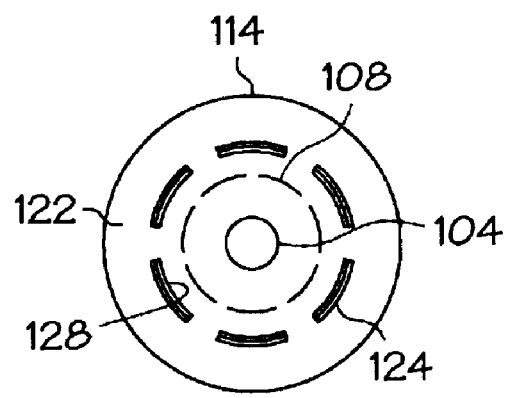
FIG. 3 is a transverse cross-sectional view of the inventive catheter of FIG. 2 taken along line 3—3.

As shown in FIG. 3, retractable sheath assembly 112 includes sheath 114 and at least one and desirably a plurality of skids 122. Skids 122 comprise an outer layer 124 of a first skid material and an inner layer 128 of a second skid material. The second skid material is different from the first skid material. The retractable sheath assembly is constructed and arranged such that the skids are disposed between the sheath and the inner member prior to, during and subsequent to retraction of the retractable sheath assembly.

Although the stent is not shown contacting the skids in FIGS. 2 and 3, the stent may rest against the skids, in particular where a self-expanding stent is used.

Sheath 114 may be made of one or more polymeric materials. Suitable polymeric materials include polyethylene, medical grade nylon, hytrel and polyether-based polyamides such as Pebax. Where Pebax is used, desirably the Pebax has a durometer of 70D or less. Other suitable materials include other balloon materials including compliant and non-compliant materials as are known in the art.

The first skid material may be polymeric. Suitable polymers include liquid crystal polymers (LCP) such as Vectran, polyetheretherketone (PEEK), polyimides including polyether imides, polysulfones, and high durometer nylon. Other suitable first skid materials include metals such as stainless steel and composite materials, for example, carbon fiber reinforced film or tape.

The second skid material may be polymeric. Suitably, the second skid material may be PTFE or fluorinated ethylene polymer (FEP). Other suitable materials for the second skid material include ceramics, amorphous carbon—desirably in the form of diamond like coatings, and ceramic—for example AlO. Desirably, the second skid material will have a coefficient of static friction of 0.1 or less on steel and more desirably, 0.04 or less on steel.

Desirably, the first skid material is harder than the second skid material as measured on the Shore D hardness scale. Also desirably, the second skid material is more slippery than the first skid material, desirably as measured by the coefficient of friction. As an example of a suitable combination of materials, the first skid material may be a hard polymeric material such as polyimide and the second skid material may be a slippery polymeric material such as PTFE.

Desirably, the combination of first and second skid materials and their relative thicknesses are chosen such that the skids are stiff enough to span the openings in a stent without protruding therein. Also desirably, the first and second skid materials and their relative thicknesses are chosen such that the stent does not impress appreciably, if at all, in the skids.

The skids may line the entire interior of the sheath or only a portion of the sheath. For example, a plurality of spaced apart skids may be provided. The invention contemplates providing any number of skids. In one embodiment, a single skid is provided. In other embodiments, two, three, four, five, six, seven, eight, nine, ten or more skids are provided.

In the embodiment of FIGS. 2 and 3, six skids 122 are provided. Skids 122 extend from sheath 114 at junctions 130. As shown in FIG. 2, skids 122 do not dimple or become partially embedded in the openings of the stent.

Figure 4:
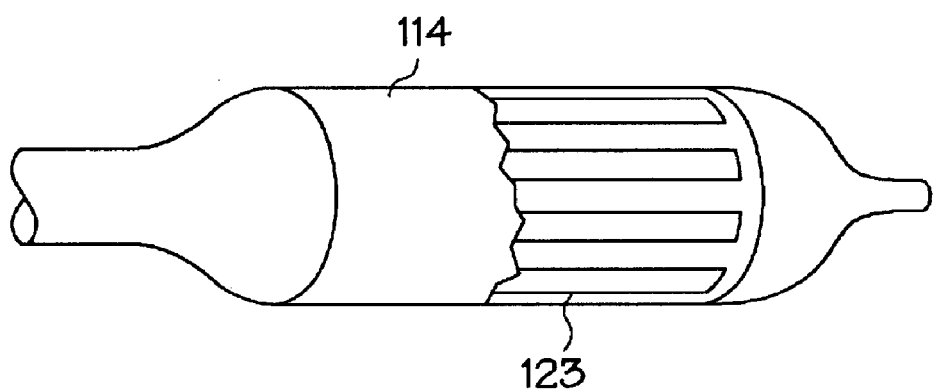
FIG. 4 is a schematic illustration of the distal end an inventive catheter with parts of the sheath cut away.
Figure 5:
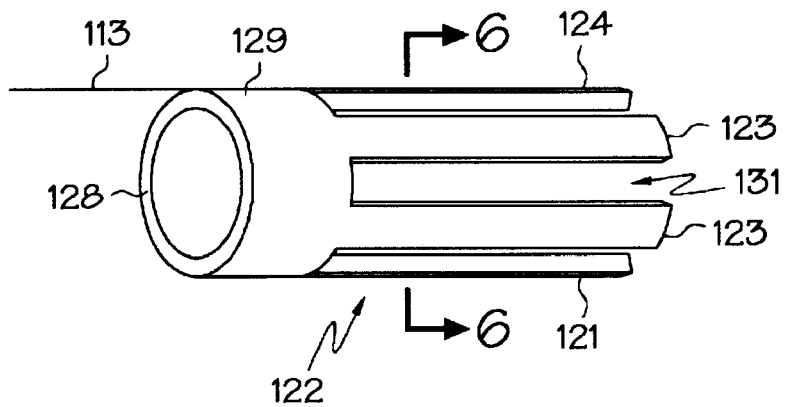
FIG. 5 is a schematic illustration of skids in the form of a tube with fingers for use in the inventive catheters.
Figure 6:
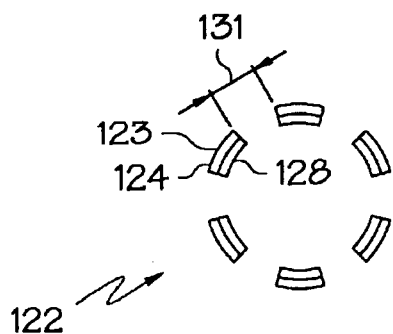
FIG. 6 is a transverse cross-sectional view of the inventive skids of FIG. 5 taken along line 6—6.

In another embodiment, as shown in FIGS. 4–6, skids 122 are in the form of a tube 121 with a plurality of fingers 123 separated by gaps 131. The fingers may be straight, curved or have straight and curved portions. As shown in FIG. 6, each finger 123 includes an outer layer 124 of a first skid material and an inner layer 128 of a second skid material. The first skid material may be any of the first skid materials disclosed above and the second skid material may be any of the second skid materials disclosed above. Fingers 123 extend from collar 129. Collar 129 is desirably as short as possible. Suitably, collar is 5 mm in length or less and more suitably, 3 mm or less. Collar 129 may be attached to sheath 114 at one or more locations. Desirably, collar 129 is positioned over a proximal or distal end portion of the medical device being delivered by the catheter.

The embodiment of FIGS. 4–6 may desirably be employed in conjunction with a retractable sheath assembly which is retracted via a pull wire. As shown in FIG. 5, pull wire 113 extends proximally from collar 129.

Figure 7:
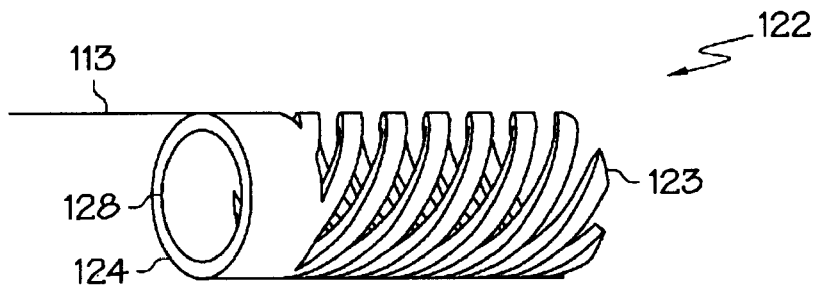
FIG. 7 is a schematic illustration of inventive spiral skids for use in the inventive catheters.

In yet another embodiment, as shown in FIG. 7, skids 122 are arranged in a spiral. Desirably the pitch of the skids is substantially similar, if not identical, to the pitch of the stent where the stent is of spiral or helical construction.

In one embodiment of the invention, each skid is attached to the tube with fingers at a single point as shown at 130 in FIG. 2. In another embodiment, the skids are attached at a plurality of locations to the tube having fingers. In yet another embodiment, the entirety of the skids is attached to the outer layer.

Figure 8:
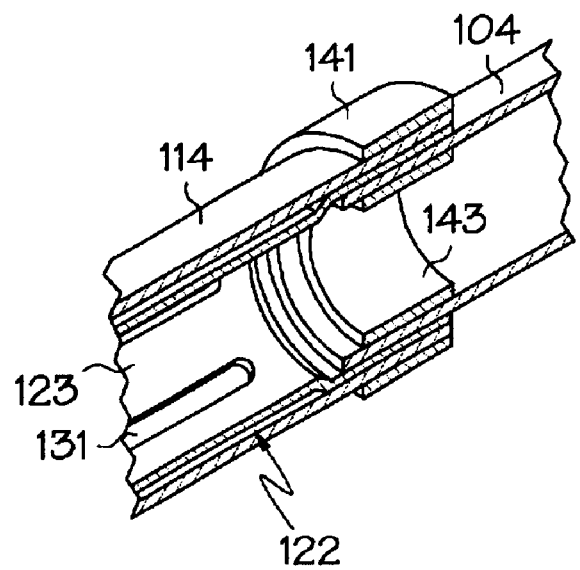
FIG. 8 is a perspective view with parts cut away of inventive skids affixed to an inner member with a ferrule.
Figure 9:
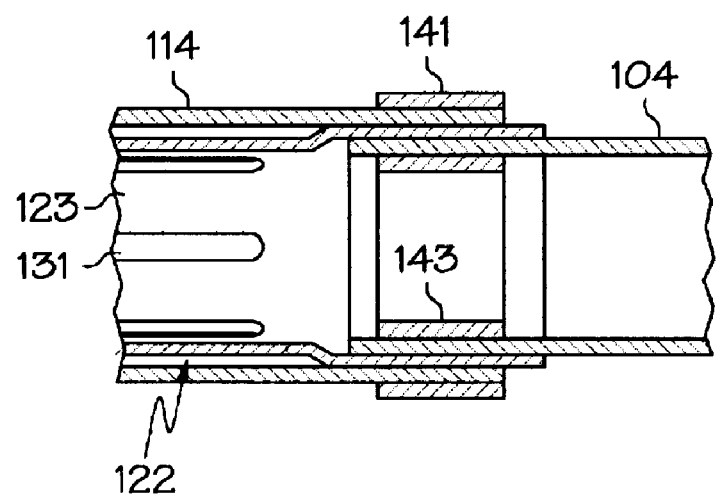
FIG. 9 is a side view with parts cut away of inventive skids affixed to an inner member with a ferrule.

Skids 122 may be bonded to sheath 114 adhesively. Suitable adhesives include UV curable adhesives such as methyl methacrylate as well as other adhesives such as epoxy, polyurethane and cyanoacrylate. Other techniques for bonding the skids to the sheath include heat bonding and laser welding techniques including those disclosed in copending, commonly assigned U.S. application Ser. No. 09/654,987. The skids may also be crimped to the sheath and held in place with ferrule 141 as shown in FIGS. 8 and 9. Ferrule 141 is disposed about retractable sheath 114, skids 122, inner member 104 and, optionally, support tube 143.

Support tube 143 may optionally be provided at the distal end of inner member 104 for additional support. The optional support tube may be disposed about inner member 104 or interior to inner member 104. A rigid marker band may also be used to hold together the sheath and skids.

Desirably, in the various embodiments of the invention, the individual skids are 0.050 inches wide or less. Also desirably, adjacent skids are separated by 0.005 inches or more. Where three skids are provided, the skids are desirably 0.045 inches wide or less and adjacent skids are separated by 0.005 inches or more. As the number of skids is increased, desirably the width of the skids is decreased. In one desirable embodiment, the individual skids are 0.025 inches wide or less and adjacent skids are separated by 0.005 inches or more. Desirably, the distance between adjacent skids will be sufficient to prevent interference between adjacent skids when the catheter is flexed in the region of the retractable sheath assembly.

Also desirably, the retractable sheath assembly is 0.004 inches thick or less and more desirably 0.002 inches thick or less. Most desirably, the retractable sheath assembly is 0.001 inches thick or less. The skids are desirably no more than 0.002 inches thick with the first skid material being no more than 0.001 inches thick and the second skid material being no more than 0.001 inches thick. Thicker skids may be appropriate under certain circumstances, for example, where very high expansion forces are encountered or where thick walled stents with large gaps are employed. Even more desirably, the skids are no more than 0.001 inches thick. Where the second skid material is made of PTFE, the PTFE is desirably no more than 0.001 inches thick and more desirably no more than 0.0001 inches thick. Where amorphous carbon, perylene or ceramic is used as the second skid material, the material is desirably no more than $1\mu$ thick.

In another embodiment, the invention is directed to a medical device catheter comprising an inner member and a retractable sheath assembly disposed about the inner member where the retractable sheath assembly has a bending flexibility of at least 1.17 GPa. Desirably, the retractable sheath assembly comprises a plurality of skids. The skids are disposed between the outer layer and the inner member. Any of the skid constructions and geometries disclosed above may be used. The retractable sheath assembly may be retracted via the use of a pull wire or any other suitable retraction mechanism. A stent or other medical device may be disposed between the inner member and the skids.

The skids may be the only covering over the optional medical device or the retractable sheath assembly may further comprise a sheath disposed about the skids and attached to the skids in one or more locations.

In accordance with the invention, the interior of the retractable sheath or exterior of the skids may be provided with an optional lubricious coating. Suitable lubricious coatings include silicones, lipids and hydrogels. Also, any of the coatings disclosed in U.S. Pat. No. 5,693,034 may be used. The coating may be used to facilitate bending of the catheter in the region of the retractable sheath by allowing the skids to slide relative to the retractable sheath.

The inventive medical device delivery systems may be provided in over-the-wire form as disclosed above as well as in fixed-wire and rapid exchange form. In the case of over the wire and rapid exchange catheters, the inner member will typically be in the form of a tube. In the case of the fixed-wire catheter, the inner member will typically be a solid, elongate structure. Additional details concerning rapid exchange and fixed-wire catheters may be found in U.S. Pat. Nos. 5,980,533 and 5,702,364.

The inventive catheters may be used in delivering medical devices such as prostheses to any suitable bodily vessel including coronary, mesentery, peripheral, or cerebral vasculature, veins, the gastrointestinal tract, the biliary tract, the urethra, the trachea, hepatic shunts and fallopian tubes. The prostheses may be stents, stent-grafts, grafts, vena cava filters or other implantable medical devices. Where the medical device delivery catheters are used to deliver stents, the stents are desirably self-expanding. Balloon expandable stents may also be delivered using the inventive medical device delivery catheters disclosed herein. Where the inventive catheters are used to deliver balloon expandable stents, the catheter may further comprise one or more socks disposed about the distal and/or proximal end of the stent. The socks may optionally be radiopaque. Additional details concerning socks may be found in copending, commonly assigned U.S. application Ser. No. 09/668,496.

The invention is also directed to inventive methods of preparing retractable sheath assemblies in particular and medical device delivery catheters in general. In one embodiment of the inventive method, a retractable sheath assembly may be made by preparing a polyimide tube, the inner diameter of which is lined with PTFE. The tube may be made by dipping coating a mandril with PTFE and subsequently, dip coating the PTFE coated mandril in polyimide. The mandril may be dip coated with one coat or, desirably, multiple coats of polyimide. The tube may then be laser cut, chemically etched, mechanically cut or otherwise cut to provide a plurality of skids with a desired spacing. The mandril may be removed from the tube prior to or subsequent to cutting the tube.

One of ordinary skill in the art will recognize that where other polymers or materials are used on the inner diameter of the skids, the process may be carried by first dipping the mandril in the other polymer or material to form the inner layer of the skid. Where materials other than polyimide are to be used on the outer diameter of the skids, the inner layer may be dip coated with any other suitable material.

The process may be modified by providing a preformed inner member of the inner material and dip coating the member to provide the outer layers of material necessary to form the skids.

The skids may also be formed coextruding the outer skid layer and the inner skid layer on an mandril. For example, any suitable stiff, rigid thermoplastic liquid crystal polymer (LCP) may be extruded over a polymeric inner layer, for example, PTFE. Examples of suitable outer skid layer materials include fiberglass, polyetheretherketone (PEEK) and polyetherimide. Other suitable materials for the inner skid layer include fluorinated ethylene polymer (FEP) and other fluorinated polymers. The resulting member may then be cut using any of the techniques disclosed above to provide the skids.

Other suitable techniques for forming the skids used in the inventive catheters include extrusion processes such as ram extrusion, polymeric casting techniques such as solvent casting and film casting, molding techniques such as blow molding, injection molding and rotational molding. Also, coating and/or plating processes including chemical vapor deposition, plasma based depositions, physical vapor deposition and electroplating may also be used in forming the skids.

The skids, however formed, may then be bonded to a retractable sheath to form a retractable sheath assembly via any of the techniques disclosed above including adhesive bonding, laser welding and crimping with a ferrule. The retractable sheath assembly may then be incorporated into the construction of a catheter using known techniques for catheter construction.

The above disclosure is intended to be illustrative and not exhaustive. This description will suggest many variations and alternatives to one of ordinary skill in this art. All these alternatives and variations are intended to be included within the scope of the claims. Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below (e.g. claim 3 may be taken as alternatively dependent from claim 1; claim 4 may be taken as alternatively dependent on claim 2, or on claim 1; claim 5 may be taken as alternatively dependent from claim 2 or claim 3; etc.).

What is claimed is:

1. A medical device delivery catheter comprising an inner member and a retractable sheath assembly disposed about the inner member, the retractable sheath assembly comprising a retractable sheath and plurality of skids extending from the retractable sheath, the skids disposed between the retractable sheath and the inner member, the skids comprising an outer layer of a first skid material and an inner layer of a second skid material different from the first material, the inner layer facing the inner member, wherein the skids have a proximal end and a distal end, the skids being connected to a collar, wherein the skids extend longitudinally from the collar.

2. The medical device delivery catheter of claim 1 further comprising a stent disposed about the inner member, the retractable sheath assembly disposed about the stent.

3. The medical device delivery catheter of claim 2 wherein the retractable sheath assembly is constructed and arranged such that the skids are disposed between the retractable sheath and the inner member prior to, during and subsequent to retraction of the retractable sheath assembly.

4. The medical device delivery catheter of claim 3 wherein the first skid material is harder than the second material.

5. The medical device delivery catheter of claim 3 wherein the second skid material has a lower coefficient of friction on steel than the first skid material.

6. The medical device delivery catheter of claim 3 wherein the first skid material is harder than the second skid material and the second skid material is more slippery than the first skid material.

7. The medical device delivery catheter of claim 3 wherein the first skid material is polyimide and the second skid material is PTFE.

8. The medical device delivery catheter of claim 3, wherein skids which are adjacent to one another are spaced from one another.

9. The medical device delivery catheter of claim 1, the retractable sheath assembly having a bending flexibility of at least 1.17 GPa.

10. The medical device delivery catheter of claim 9 the first skid material having a shore D hardness of at least 84.

11. The medical device delivery catheter of claim 10 wherein the sheath is attached to the skids.

12. The medical device delivery catheter of claim 11 further comprising a stent disposed about the inner member, the retractable sheath assembly disposed about the stent.

13. The medical device delivery catheter of claim 12 wherein the stent is self-expanding.

14. The medical device delivery catheter of claim 1, wherein the collar is connected to the retractable sheath.

15. The medical device delivery catheter of claim 14, wherein the skids spiral about the inner member.

16. A medical device delivery catheter comprising an inner member and a retractable sheath assembly, the retractable sheath assembly having a thickness of no more than 0.002 inches, wherein the retractable sheath assembly comprises a retractable sheath and one or more skids attached to the retractable sheath, the one or more skids disposed between the retractable sheath and the inner member, wherein the skids have a proximal end and a distal and, the skids being connected to a collar, wherein the skids extend longitudinally from the collar.

17. The medical device delivery system of claim 16 further comprising a stent disposed about the inner member, the retractable sheath assembly disposed about the stent.

18. The medical device delivery system of claim 17 comprising a plurality of skids, each skid having an outer layer of a first skid material and an inner layer of a second skid material, the first skid material harder than the second skid material.

19. The medical device delivery system of claim 18 wherein the second skid material is more slippery than the first skid material.

20. The medical device delivery system of claim 16 comprising a plurality of skids.

21. The medical device delivery catheter of claim 16, wherein the collar is connected to the retractable sheath.

22. The medical device delivery catheter of claim 21, wherein the skids spiral about the inner member.

* * * * *